United States Patent
Yamaguchi et al.

(10) Patent No.: US 9,014,772 B2
(45) Date of Patent: Apr. 21, 2015

(54) BLOOD INFORMATION MEASURING METHOD AND APPARATUS

(75) Inventors: Hiroshi Yamaguchi, Kanagawa (JP); Takaaki Saito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 158 days.

(21) Appl. No.: 13/434,924

(22) Filed: Mar. 30, 2012

(65) Prior Publication Data
US 2012/0253157 A1    Oct. 4, 2012

(30) Foreign Application Priority Data
Apr. 1, 2011    (JP) .................................. 2011-081754

(51) Int. Cl.
| | | |
|---|---|---|
| *A61B 5/1455* | (2006.01) | |
| *A61B 1/06* | (2006.01) | |
| *A61B 5/06* | (2006.01) | |
| *A61B 5/1459* | (2006.01) | |

(52) U.S. Cl.
CPC ........... *A61B 5/14551* (2013.01); *A61B 1/0638* (2013.01); *A61B 5/065* (2013.01); *A61B 5/1459* (2013.01); *A61B 1/0646* (2013.01)

(58) Field of Classification Search
CPC . A61B 5/1455; A61B 5/14551; A61B 5/1459
USPC .................................................. 600/309–344
See application file for complete search history.

(56) References Cited

U.S. PATENT DOCUMENTS

| | | | |
|---|---|---|---|
| 5,001,556 A | | 3/1991 | Nakamura et al. |
| 6,256,530 B1 | * | 7/2001 | Wolfe ............................ 600/477 |
| 6,350,261 B1 | * | 2/2002 | Domankevitz et al. .......... 606/17 |
| 2008/0281154 A1 | | 11/2008 | Gono et al. |
| 2010/0036260 A1 | * | 2/2010 | Zuluaga et al. ................ 600/476 |

FOREIGN PATENT DOCUMENTS

| | | |
|---|---|---|
| JP | 1-308531 A | 12/1989 |
| JP | 6-315477 A | 11/1994 |
| JP | 2000-262459 A | 9/2000 |

* cited by examiner

*Primary Examiner* — Eric Winakur
*Assistant Examiner* — Marjan Fardanesh
(74) *Attorney, Agent, or Firm* — Birch, Stewart, Kolasch & Birch, LLP

(57) ABSTRACT

In a special mode, a superficial wavelength set having plural types of narrow band light in a blue wavelength band of 400 to 500 nm is chosen. The plural types of narrow band light are successively applied to an internal body portion. A CCD captures images of the internal body portion under the narrow band light. A blood information calculation section calculates an oxygen saturation level of hemoglobin in a blood vessel based on an image signal. A comparison section compares the calculated oxygen saturation level with a predetermined threshold value. When the oxygen saturation level is less than the threshold value, a hypoxic region detection signal is outputted to a wavelength set switching section. The wavelength set switching section switches from the superficial wavelength set to a middle wavelength set and to a deep wavelength set, so the oxygen saturation levels at middle and deep depths are measured.

13 Claims, 11 Drawing Sheets

| DEPTH | WAVELENGTH SET (nm) |
|---|---|
| SUPERFICIAL LAYER | 405、445、473 |
| MIDDLE LAYER | 540、550、580 |
| DEEP LAYER | 680、805、950 |

Gb (SUPERFICIAL LAYER)   Gg (MIDDLE LAYER)   Gr (DEEP LAYER)

Gb (SUPERFICIAL LAYER)   Gg (MIDDLE LAYER)   Gr (DEEP LAYER)

BLOOD INFORMATION MEASURING METHOD AND APPARATUS

BACKGROUND OF THE INVENTION

1. Field of the Invention

The present invention relates to a blood information measuring method and apparatus for measuring blood information from an image signal of a blood vessel.

2. Description Related to the Prior Art

Endoscopes are widely used for observation of a lesion located inside a human body. The endoscope is provided with an insert section to be introduced into the human body, and a handling section for steering the insert section. The insert section has a lighting window and an imaging window at its distal end. An internal body portion is imaged through the imaging window while being illuminated with light through the lighting window, and an obtained endoscopic image is displayed on a monitor.

As a light source of the endoscope, a white light source such as a xenon lamp or a metal halide lamp is conventionally available. Additionally, there is a method recently in the limelight in which light (narrow band light) of a narrow wavelength band is used as illumination light to facilitate finding out the lesion (refer to US Patent Application Publication No. 2008/0281154 corresponding to Japanese Patent No. 3583731).

Also, there is studied a method for measuring information of blood flowing through a blood vessel, for example, an oxygen saturation level of hemoglobin, a blood flow, and the like (refer to Japanese Patent Laid-Open Publication No. 06-315477). In this method, the blood vessel is extracted from the endoscopic image captured under the narrow band light, and the blood information is obtained from an image signal. This method uses the illumination light of each wavelength band of 300 to 400 nm, in the vicinity of 400 nm, 400 to 500 nm, 500 to 600 nm, 450 to 850 nm, and the like. Taking the case of measuring the oxygen saturation level of the hemoglobin as an example, an optimal wavelength band is chosen from the five wavelength bands in accordance with the internal body portion to be examined. In this chosen wavelength band, two wavelengths are used as a wavelength set, including a measurement wavelength at which absorbance much varies with the oxygen saturation level of the hemoglobin and a reference wavelength at which the absorbance hardly varies therewith. Two types of light having different wavelengths are applied to the internal body portion in succession. Then, an image signal obtained under the light of the measurement wavelength is corrected using an image signal obtained under the light of the reference wavelength, in order to calculate the oxygen saturation level of the blood through the blood vessel.

By the way, how deep light penetrates into human tissue depends on a wavelength band of the light. Taking advantage of this property, the depth of the lesion such as cancer can be inspected. More specifically, switching among the wavelength sets makes it possible to measure the oxygen saturation level of the blood flowing through the blood vessels in different layers of mucosa from a mucosal surface to a submucosal layer. This allows inspection of the depth or spread of the cancer.

The Japanese Patent Laid-Open Publication No. 06-315477 does not specifically disclose switching timing of the wavelength sets. If the switching is performed manually, complicated operation is required. Furthermore, since the manual switching tends to take long time, the observed portion happens to move. In the case of automatic switching, on the other hand, the switching is performed even during observation of a normal portion where no switching is required. Thereby, the oxygen saturation level is calculated in vain.

SUMMARY OF THE INVENTION

An object of the present invention is to provide a blood information measuring method and apparatus that can perform switching among wavelength sets easily and appropriately.

A blood information measuring apparatus according to the present invention includes a lighting section, an imaging section, a wavelength tunable element, a blood information calculation section, a comparison section, a wavelength set switching section, and a monitor. The lighting section applies illumination light to an internal body portion having a blood vessel. The imaging section performs photoelectric conversion of reflected light from the internal body portion irradiated with the illumination light and outputs an image signal. The wavelength tunable element narrows a wavelength band of the illumination light to be applied to the internal body portion or the reflected light to be incident on the imaging section in accordance with one of plural wavelength sets. The blood information calculation section calculates blood information of blood flowing through the blood vessel based on the image signal. The comparison section compares the calculated blood information with a threshold value. The wavelength set switching section controls the wavelength tunable element so as to switch among the wavelength sets in accordance with a comparison result of the comparison section. Each wavelength set includes plural types of narrow band light that penetrate to similar depths into the internal body portion. The monitor displays the blood information measured with each wavelength set.

The blood information is preferably an oxygen saturation level of hemoglobin calculated based on absorbance.

The wavelength set preferably includes at least one type of narrow band light having a wavelength at which there is a difference in an absorption coefficient between oxygenated hemoglobin and deoxygenated hemoglobin, and at least one type of narrow band light having a wavelength at which there is no difference in the absorption coefficient between the oxygenated hemoglobin and the deoxygenated hemoglobin.

The wavelength set switching section preferably chooses one of the plural wavelength sets as an abnormality detection wavelength set used for detection of an abnormal region. When the oxygen saturation level measured with the abnormality detection wavelength set is less than the threshold value, the comparison section preferably outputs an abnormal region detection signal. The wavelength set switching section preferably switches in response to the abnormal region detection signal from the abnormality detection wavelength set to one of the other wavelength sets, to measure the oxygen saturation level of the blood flowing through the blood vessel at a different depth.

The wavelength set switching section may successively switch among the wavelength sets to measure the oxygen saturation level with every wavelength set, and thereafter choose the abnormality detection wavelength set again.

One of the plural wavelength sets may be a superficial wavelength set having the plural types of narrow band light in a blue wavelength band of 400 to 500 nm. The superficial wavelength set may be used as the abnormality detection wavelength set.

The blood information measuring apparatus may further include a location detecting section for detecting a location of the internal body portion within a body. The abnormality detection wavelength set may be chosen from the plural wavelength sets in accordance with this location. The location detecting section may detect the location of the internal body portion by applying an image recognition process to an image of the internal body portion.

The plural wavelength sets may further include a middle wavelength set having the plural types of narrow band light in a green wavelength band of 500 to 600 nm. When the location detecting section detects that the internal body portion is located in esophagus or large intestine, the superficial wavelength set may be chosen as the abnormality detection wavelength set. When the location detecting section detects that the internal body portion is located in stomach, the middle wavelength set may be chosen as the abnormality detection wavelength set.

The lighting section may emit white light in a broad wavelength band as the illumination light. The wavelength tunable element may be disposed in the lighting section to narrow the wavelength band of the illumination light, or may be disposed in the imaging section to narrow the wavelength band of the reflected light.

The monitor may display calculation results of the oxygen saturation level obtained with switching among the plural wavelength sets simultaneously in a tiled manner or separately on different screens on a wavelength set basis.

The wavelength sets may further include a deep wavelength set having the plural types of narrow band light in a red wavelength band of 600 to 1000 nm.

The blood information measuring apparatus may further include a mode switch for switching between a normal mode and a special mode. In the normal mode, white light in a broad wavelength band may be applied to the internal body portion, and an image may be produced from the image signal obtained under the white light and displayed on the monitor. In the special mode, the oxygen saturation level may be calculated, and a calculation result may be displayed on the monitor.

A blood information measuring method according to the present invention includes the steps of applying illumination light to an internal body portion; performing photoelectric conversion of reflected light from the internal body portion irradiated with the illumination light, and outputting an image signal; narrowing a wavelength band of the illumination light to be applied to the internal body portion or the reflected light in accordance with one of plural wavelength sets; calculating blood information of blood flowing through a blood vessel based on the image signal; comparing the calculated blood information with a threshold value; and switching among the plural wavelength sets in accordance with a comparison result. Each wavelength set includes plural types of narrow band light that penetrate to similar depths into the internal body portion.

According to the present invention, the switching among the plural wavelength sets can be performed easily and appropriately in accordance with the measured blood information. Therefore, it is possible to easily measure the blood information with respect to a depth direction of tissue.

BRIEF DESCRIPTION OF THE DRAWINGS

For more complete understanding of the present invention, and the advantage thereof, reference is now made to the following descriptions taken in conjunction with the accompanying drawings, in which.

DESCRIPTION OF THE PREFERRED EMBODIMENTS

Figure 1:
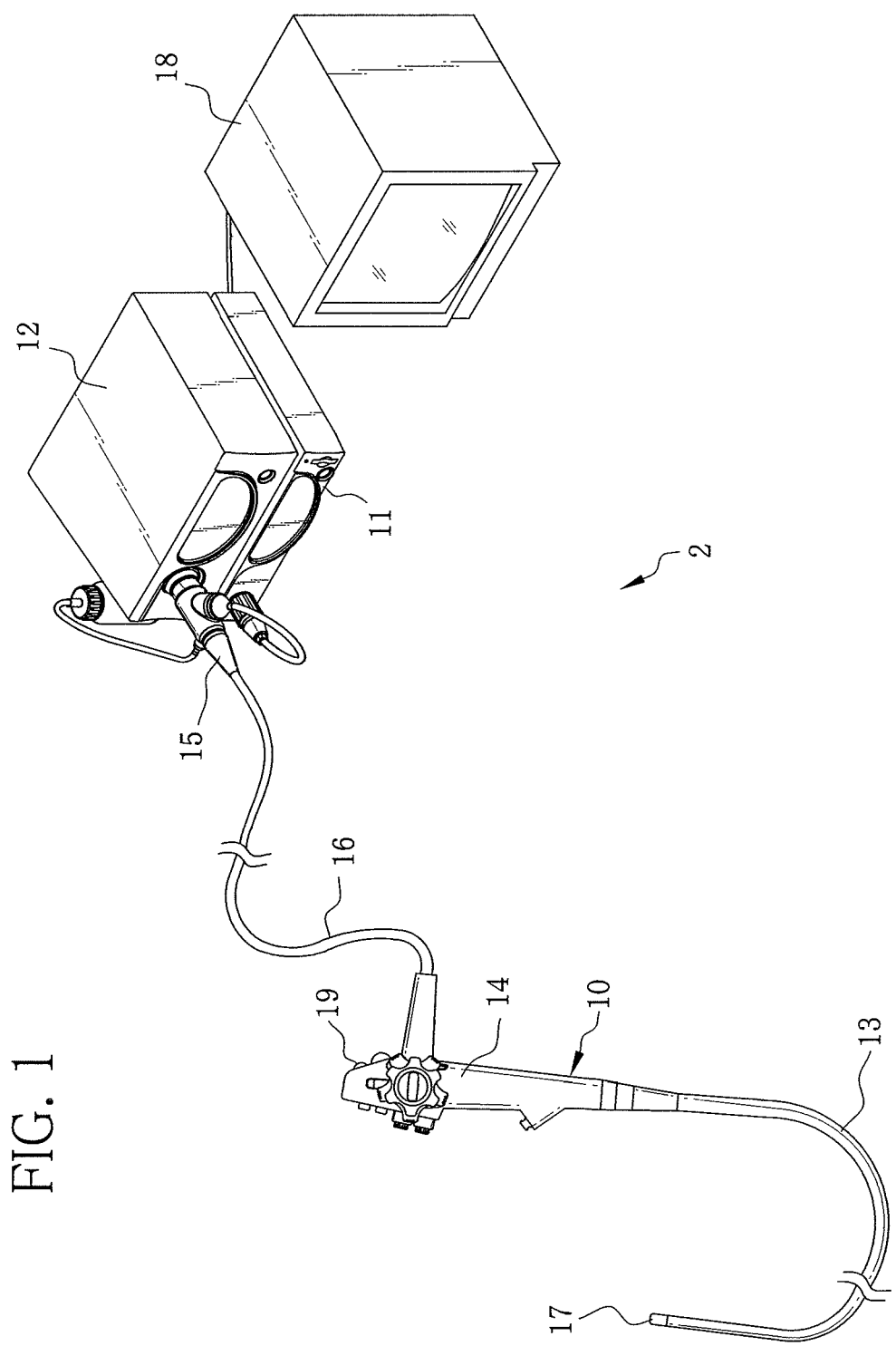
FIG. 1 is an external view of a blood information measuring apparatus.

As shown in FIG. 1, a blood information measuring apparatus 2 is constituted of an electronic endoscope 10, a processor device 11, and a light source device 12. As is widely known, the electronic endoscope 10 includes a flexible insert section 13 to be introduced into a body of a patient, a handling section 14 coupled to a base end of the insert section 13, a connector 15 connected to the processor device 11 and the light source device 12, and a universal cord 16 for connecting between the handling section 14 and the connector 15. Note that, the blood information measuring apparatus 2 is identical to a well-known electronic endoscope apparatus, except that an image processor and a CPU of the processor device 11 have the additional function of measuring blood information.

The handling section 14 is provided with various operation members, including an angle knob for flexibly bending a distal end portion 17 of the insert section 13 upward and downward and from side to side, an air/water supply button for ejecting air and water from an air/water supply nozzle, a release button for capturing a still observation image (endoscopic image), and the like.

The handling section 14 has a medical instrument inlet on its front end side. Into the medical instrument inlet, a medical instrument such as forceps or an electric cautery is inserted. The medical instrument inlet is coupled to a medical instrument outlet provided at the distal end portion 17 through a channel provided in the insert section 13.

The processor device 11 is electrically connected to the light source device 12 with a cable, and performs centralized control of the blood information measuring apparatus 2. The processor device 11 supplies power to the electronic endoscope 10 through a transmission cable routed through the universal cord 16 and the insert section 13, and controls operation of a CCD 33 (see FIG. 2) provided at the distal end portion 17. The processor device 11 receives an image signal outputted from the CCD 33 through the transmission cable, and applies various processes to the received image signal to produce image data. The image data produced in the processor device 11 is sent to a monitor 18 connected to the processor device 11 with a cable, so an observation image is displayed on a screen of the monitor 18.

The blood information measuring apparatus 2 has a normal mode for observing an internal body portion under illumination with white light, and a special mode for calculating blood information with application of narrow band light to the internal body portion. Mode switching is performed by operating a mode switch 19. The blood information measuring apparatus 2 is automatically put into the normal mode immediately after turning the power on by a command from the processor device 11.

Figure 2:
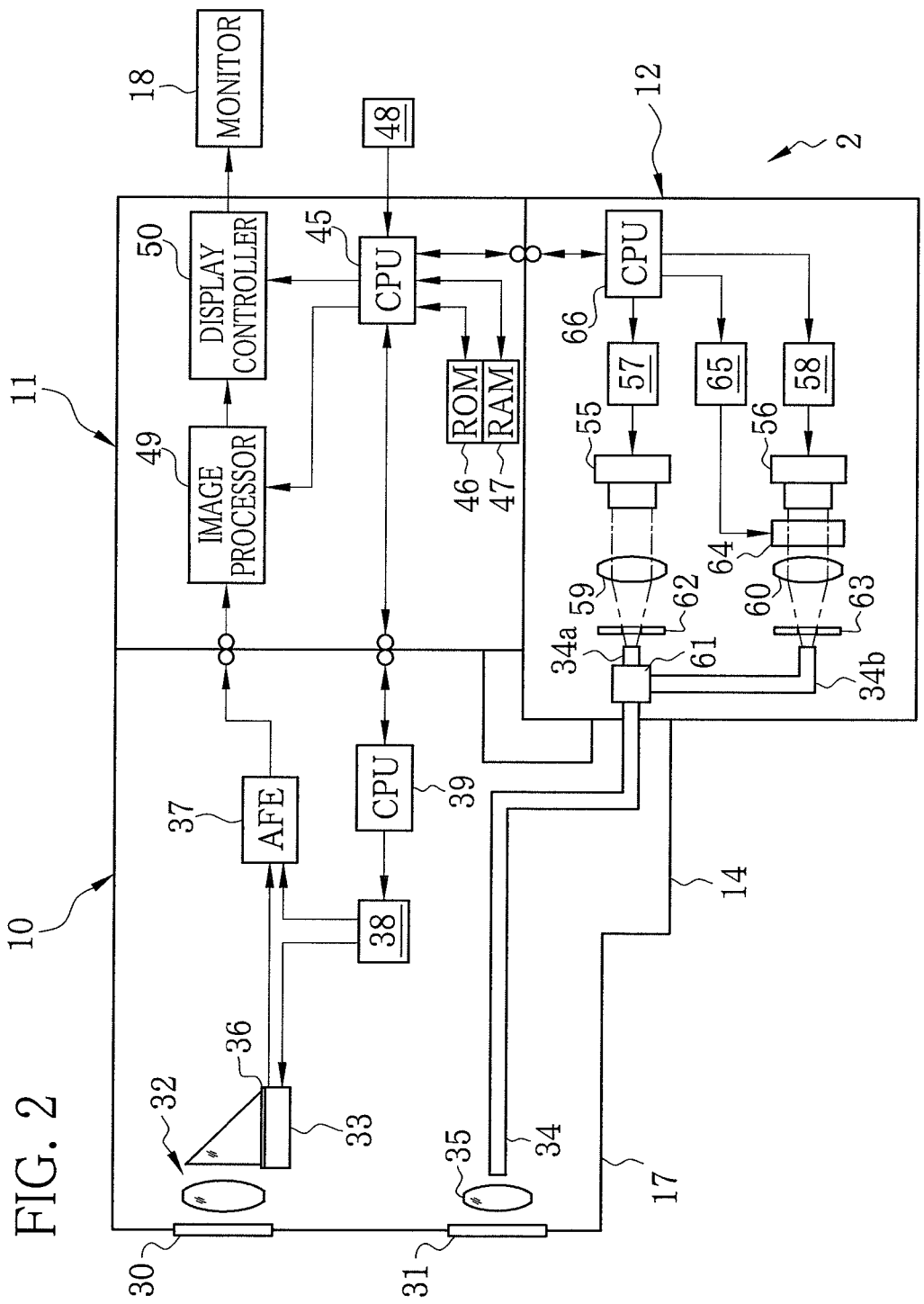
FIG. 2 is a block diagram of the blood information measuring apparatus.

In FIG. 2, the distal end portion 17 has an imaging window 30, a lighting window 31, and the like. The CCD 33 for imaging the inside of the body is disposed in the recess of the imaging window 30 through the medium of an objective optical system 32 including a lens group and a prism. Illumination light is emitted from the light source device 12 and guided through a light guide 34 routed through the universal cord 16 and the insert section 13, and is applied through a lighting lens 35 and the lighting window 31 to the internal body portion.

Figure 3:
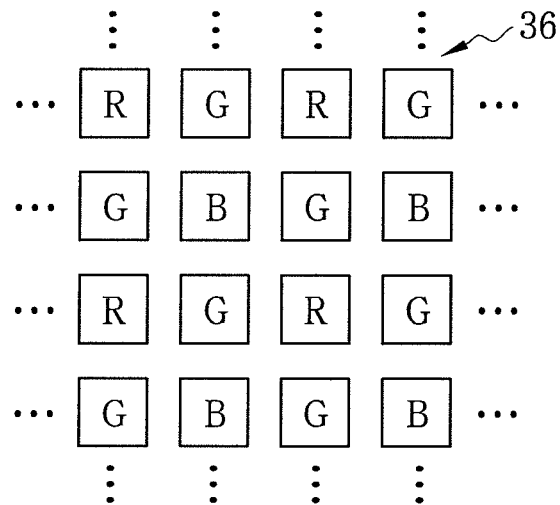
FIG. 3 is an explanatory view of a color filter of a Bayer arrangement.
Figure 4:
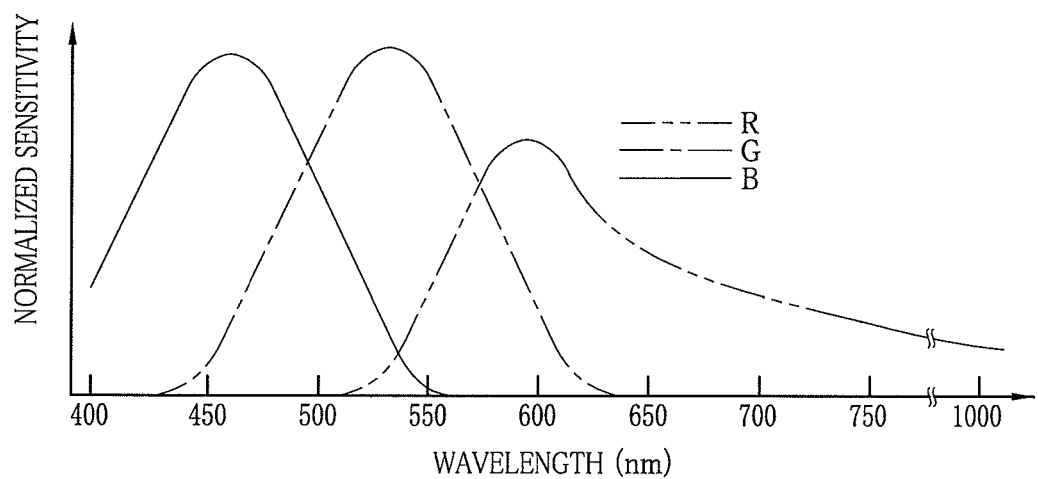
FIG. 4 is a graph showing sensitivity spectra of each of R, G, and B pixels of a CCD.

The illumination light is reflected from the internal body portion, and is incident on the CCD 33 through the imaging window 30 and the objective optical system 32. The CCD 33 performs photoelectric conversion of the reflected light, and outputs the image signal. In an imaging plane of the CCD 33, there is formed a color filter having plural color segments, for example, a RGB (red, green, and blue) primary color filter 36 of a Bayer arrangement, as shown in FIG. 3. FIG. 4 shows sensitivity spectra of each of R, G, and B pixels of the CCD 33 ascribable to spectral transmittance of the primary color filter 36 and spectral sensitivity of the pixels themselves. The R pixel has a sensitivity peak in the vicinity of 600 nm. The G pixel has a sensitivity peak in the vicinity of 530 nm. The B pixel has a sensitivity peak in the vicinity of 460 nm. The R pixel has broad spectral sensitivity, and is sensitive to light having wavelengths even in an infrared range in the vicinity of approximately 1000 nm.

An analog frontend processor (AFE) 37 includes a correlated double sampling circuit (CDS), an automatic gain controller (AGC), and an analog-to-digital converter (A/D). The CDS applies a correlated double sampling process to the image signal outputted from the CCD 33, to remove reset noise and amplification noise occurring in the CCD 33. The AGC amplifies the image signal after the noise removal by the CDS with a gain (amplification factor) specified by the processor device 11. The A/D converts the image signal amplified by the AGC into a digital signal of a predetermined bit number. The image signal digitized by the A/D is inputted through the transmission cable to an image processor 49 of the processor device 11.

A CCD driver 38 generates a drive pulse (vertical/horizontal scan pulse, electronic shutter pulse, readout pulse, reset pulse, and the like) of the CCD 33 and a synchronization pulse of the AFE 37. The CCD 33 carries out image capturing operation in response to the drive pulse from the CCD driver 38, and outputs the image signal. Each part of the AFE 37 operates based on the synchronization pulse from the CCD driver 38.

After the electronic endoscope 10 is connected to the processor device 11, a CPU 39 actuates the CCD driver 38 in response to an operation start command from a CPU 45 of the processor device 11, and adjusts the gain of the AGC of the AFE 37 through the CCD driver 38.

The CPU 45 performs centralized control of the entire processor device 11. The CPU 45 is connected to every part through a data bus, an address bus, and control lines (all not shown). A ROM 46 stores various programs (OS, application programs, and the like) and data (graphic data and the like) for controlling operation of the processor device 11. The CPU 45 reads out the necessary programs and the data from the ROM 46, and loads the programs to a RAM 47 being a working memory, and runs the programs in sequence. The CPU 45 also obtains information varying from examination to examination such as text data including an examination date, a patient's name, and a doctor's name from an operation panel of the processor device 11 or through a network e.g. a LAN (local area network), and writes the information to the RAM 47.

An operation unit 48 is a well-known input device including the operation panel provided on a cabinet of the processor device 11, a mouse, and a keyboard. The CPU 45 operates each part in response to operation signals from the operation unit 48 and from the release button and the mode switch 19 provided on the handling section 14 of the electronic endoscope 10.

The image processor 49 calculates the blood information, as described later in detail, in addition to subjecting the image signal inputted from the electronic endoscope 10 to various image processes such as color interpolation, white balance adjustment, gamma correction, image enhancement, image noise reduction, and color conversion.

A display controller 50 receives the graphic data from the ROM 46 and the RAM 47 through the CPU 45. The graphic data includes a display mask for covering an ineffective pixel area of the observation image to expose only an effective pixel area, the text data such as the examination date, the patient's name, the doctor's name, and an examination mode name chosen at the present time, a graphical user interface (GUI), and the like. The display controller 50 performs various display control processes. More specifically, the display controller 50 overlays the display mask, the text data, and the GUI on an image from the image processor 49, and draws the image after the overlaying process on the screen of the monitor 18.

The display controller 50 has a frame memory for temporarily storing the image from the image processor 49. The display controller 50 reads out the image from the frame memory, and converts the read image into a video signal (component signal, composite signal, and the like) compatible with a display format of the monitor 18. Thus, the observation image is displayed on the monitor 18.

Besides the components described above, the processor device 11 is provided with a compression circuit for compressing the image in a predetermined compression format (for example, a JPEG format), a media interface for writing the compressed image to a removable medium such as a CF card, a magneto-optical disk (MO), or a CD-R, a network interface for controlling transmission of various types of data through a network such as the LAN, and the like. The compression circuit, the media interface, and the network interface are connected to the CPU 45 via the data bus.

The light source device 12 has a first light source 55 and a second light source 56. The first and second light sources 55 and 56 have identical structure, and have a xenon lamp, a halogen lamp, a white LED (light emitting diode), or the like that emits white light of a broad wavelength band extending from blue to red, from 400 nm to 1000 nm, for example. Alternatively, as the first and second light sources 55 and 56, another light source may be used that emits the white light by mixing semiconductor laser light being blue or ultraviolet excitation light with green to yellow to red fluorescence emitted from a phosphor by excitation.

The first and second light sources 55 and 56 are driven by light source drives 57 and 58, respectively. A condenser lens 59 gathers the light emitted from the first light source 55, and leads the light into a light guide 34a disposed on a light exit side of the first light source 55. A condenser lens 60 gathers the light emitted from the second light source 56, and leads the light into a light guide 34b disposed on a light exit side of the second light source 56. The light guides 34a and 34b are coupled to the single light guide 34 via a coupler 61. A variable aperture stop 62 is disposed between the condenser lens 59 and the light guide 34a to adjust the amount of light to be incident upon a light entrance of the light guide 34a, and a variable aperture stop 63 is disposed between the condenser lens 60 and the light guide 34b to adjust the amount of light to be incident upon a light entrance of the light guide 34b. Instead of provision of the coupler 61, each of the two light sources 55 and 56 may be provided with a light guide, to transmit the light separately to the lighting window 31.

A wavelength tunable element 64 is disposed between the second light source 56 and the condenser lens 60. The wavelength tunable element 64 is driven by an element driver 65 to change a wavelength band of light to be transmitted therethrough. As the wavelength tunable element 64, an etalon is usable in which operating an actuator e.g. a piezoelectric element varies a surface distance between two boards made of high reflective filters, so as to control the wavelength band of the light to be transmitted. In another case, a liquid crystal tunable filter is usable in which a birefringent filter and a nematic liquid crystal cell are sandwiched between polarizing filters, and varying an impressed voltage to the liquid crystal cell controls the wavelength band of the light to be transmitted. In further another case, a rotary filter into which plural interference filters (band pass filters) are combined may be used as the wavelength tunable element 64.

A CPU 66 of the light source device 12 communicates with the CPU 45 of the processor device 11. The CPU 66 performs turn-on and -off control of the laser light from each individual light source 55, 56 and light amount control by each individual variable aperture stop 62, 63 through the light source drivers 57 and 58. Also, the CPU 66 controls the operation of the wavelength tunable element 64 through the element driver 65.

When the normal mode is chosen, the CPU 45 controls the operation of the light source driver 57 through the CPU 66 so as to turn on only the first light source 55. Thus, only the white light is applied to the internal body portion. When the special mode is chosen, the second light source 56 is turned on, while the first light source 55 is turned off. Thus, only the narrow band light filtered through the wavelength tunable element 64 is applied to the internal body portion.

Figure 5:
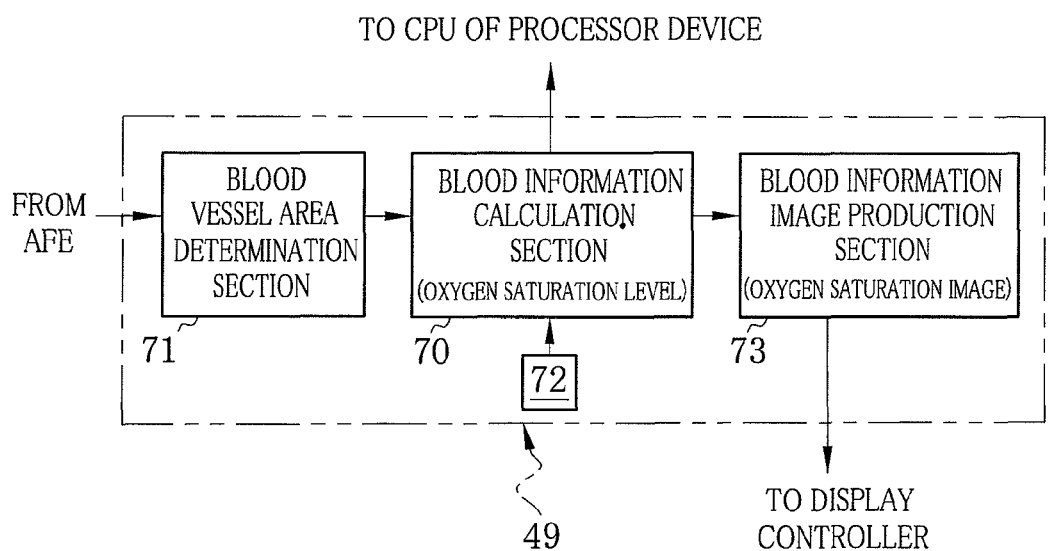
FIG. 5 is a block diagram of an image processor.

As shown in FIG. 5, the image processor 49 has a blood vessel area determination section 71, a blood information calculation section (oxygen saturation level calculation section) 70, and a blood information image production section (oxygen saturation image production section) 73. The blood vessel area determination section 71 analyzes the image inputted from the AFE 37, and determines (extracts) an area of a blood vessel in the image by referring to difference in a luminance value between the blood vessel area and the other area, for example. The blood information calculation section 70 calculates the blood information from the image signal of the determined blood vessel area. The blood information includes an oxygen saturation level of hemoglobin, a blood flow, a depth of the blood vessel, and the like. In this embodiment, the oxygen saturation level of the hemoglobin is measured.

Figure 6:
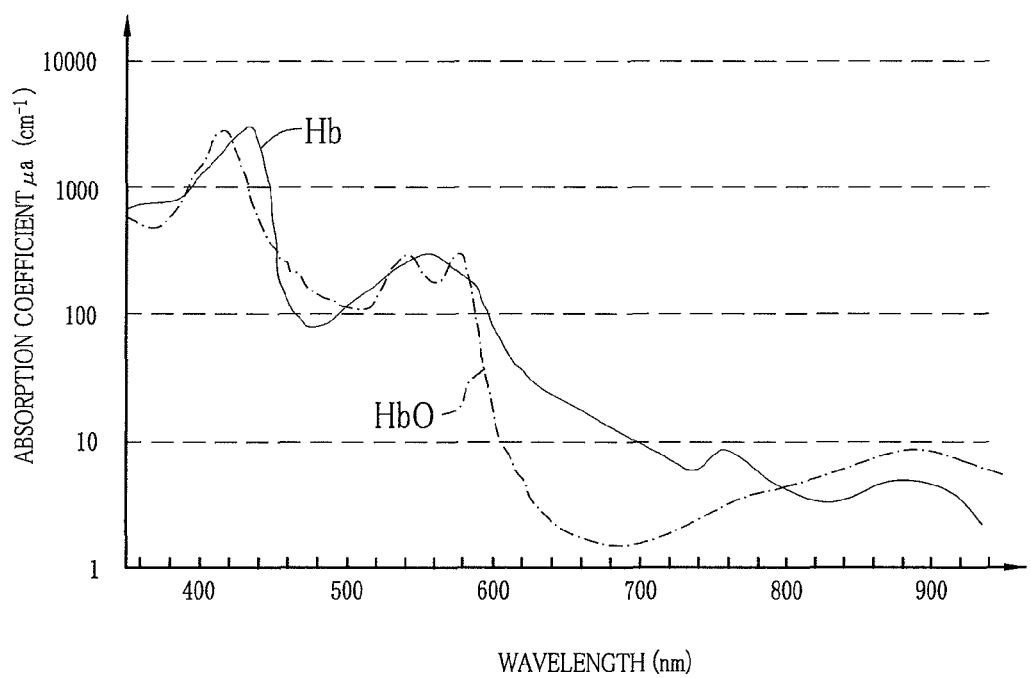
FIG. 6 is a graph showing absorption spectra of oxygenated hemoglobin and deoxygenated hemoglobin.

As shown in FIG. 6, an absorption coefficient $\mu a$ of the hemoglobin varies with a wavelength of the illumination light. The absorption coefficient $\mu a$ represents the magnitude (absorbance) of light absorbed by the hemoglobin, and is a coefficient of an expression of $I_0 \exp(-\mu a \times x)$, which represents attenuation of light applied to the hemoglobin. Note that, $I_0$ denotes intensity of the illumination light, and x(cm) denotes the depth to the blood vessel from a surface of the internal body portion.

An absorption spectrum of deoxygenated hemoglobin Hb not being bonded to oxygen is different from that of oxygenated hemoglobin HbO being bonded to oxygen. The deoxygenated hemoglobin Hb and the oxygenated hemoglobin HbO have the different absorption coefficients $\mu a$ except at isosbestic points (intersection points of the absorption spectra of Hb and HbO) at which the deoxygenated hemoglobin Hb and the oxygenated hemoglobin HbO have the same absorption coefficient $\mu a$.

The difference in the absorption coefficient $\mu a$ causes variation in the intensity of the reflected light, even if light of the same intensity and the same wavelength is applied to the same blood vessel. If light of the same intensity and different wavelengths is applied, the intensity of the reflected light is varied, because the absorption coefficient $\mu a$ depends on the wavelength. For this reason, analyzing plural images that are captured under irradiation with plural types of narrow band light of different wavelength bands makes it possible to obtain a ratio between the oxygenated hemoglobin and the deoxygenated hemoglobin in the blood vessel, that is, information of the oxygen saturation level.

The blood information calculation section 70 has a frame memory (not shown) that temporarily stores the plural images captured under the plural types of narrow band light of different wavelength bands. The blood information calculation section 70 reads out each image from the frame memory, and calculates image parameters e.g. the absorbance by various arithmetic operations using the image signal of the blood vessel area determined in each image by the blood vessel area determination section 71, for example, from a ratio or difference in the image signal (pixel value) of the same pigment between frames. By way of example, when first to third narrow band light is successively applied to the internal body portion, and the oxygen saturation level is calculated from first to third frames G1 to G3 captured under the first to third narrow band light, the blood information calculation section 70 calculates G1/G3 and G2/G3 as the image parameters.

Figure 7:
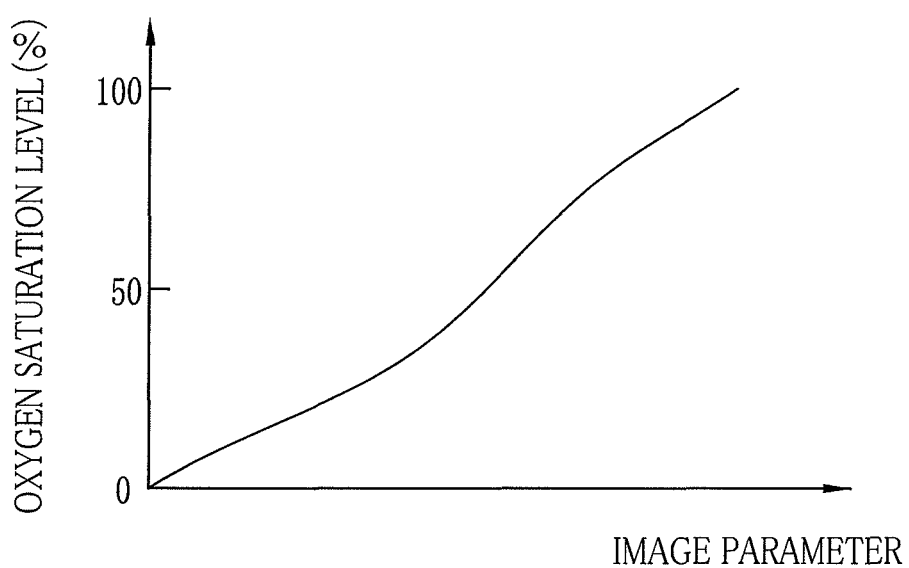
FIG. 7 is a graph showing an example of reference data.

Reference data 72 includes a function or a data table representing the relation between the image parameters and the oxygen saturation level, as shown in FIG. 7, on a wavelength set basis. The relation between the image parameters and the oxygen saturation level is obtained in advance by experiment and the like. The blood information calculation section 70 obtains the oxygen saturation level corresponding to the image parameters from the reference data 72 by substitution of the calculated image parameters into the function or a lookup on the data table. Then, a calculation result of the oxygen saturation level is outputted to the blood information image production section 73 and the CPU 45.

The blood information image production section 73 produces an oxygen saturation image in which the calculation result is reflected based on a color map for displaying the calculation result of the blood information calculation section 70 with artificial colors. The oxygen saturation image has text data of a value of the oxygen saturation level, which the blood information calculation section 70 calculates from the reference data 72. According to the color map, for example, cyan is assigned to a hypoxic region having the relative low oxygen saturation level. Magenta is assigned to a middle region having the middle oxygen saturation level, and yellow is assigned to a hyperoxic region having the relatively high oxygen saturation level.

Figures 8, 9:
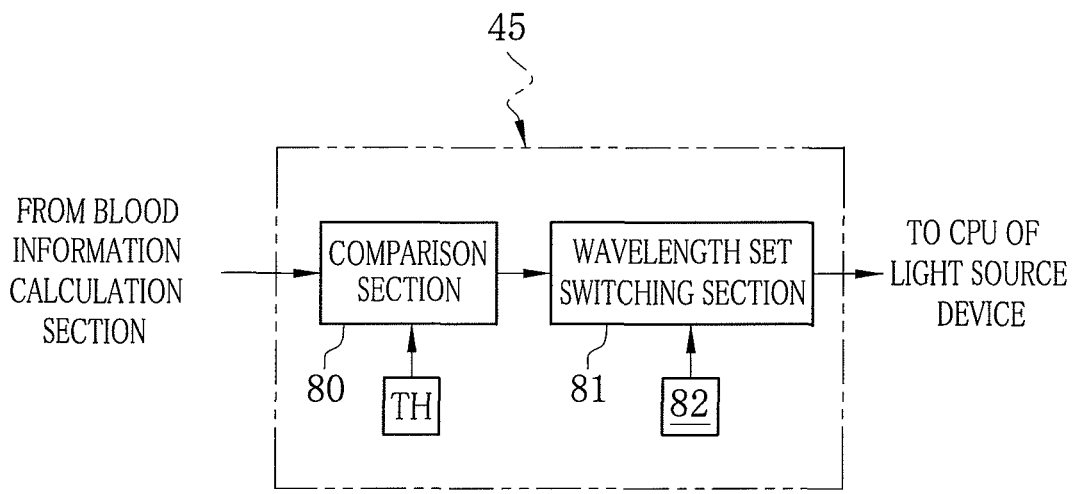
FIG. 8 is a block diagram showing structure of a CPU of a processor device.
FIG. 9 is an example of a wavelength set table.

As shown in FIG. 8, running the program stored in the ROM 46 makes the CPU 45 function as a comparison section 80 and a wavelength set switching section 81. The comparison section 80 compares the calculation result of the oxygen saturation level from the blood information calculation section 70 with a threshold value TH stored in advance on the ROM 46. The threshold value TH is set at a value that typical cancer tissue indicates, and is determined from examination data accumulated in past. When the calculation result of the oxygen saturation level is the threshold value TH or more, the comparison section 80 judges that no cancer tissue exists, and performs no additional examination (measurement). On the other hand, when the calculation result of the oxygen saturation level is less than the threshold value TH, the comparison section 80 judges that cancer tissue exists. In this case, the comparison section 80 outputs a hypoxic region detection signal, which indicates the existence of the cancer tissue, to the wavelength set switching section 81, and continues the additional examination of the cancer tissue.

Figure 10:
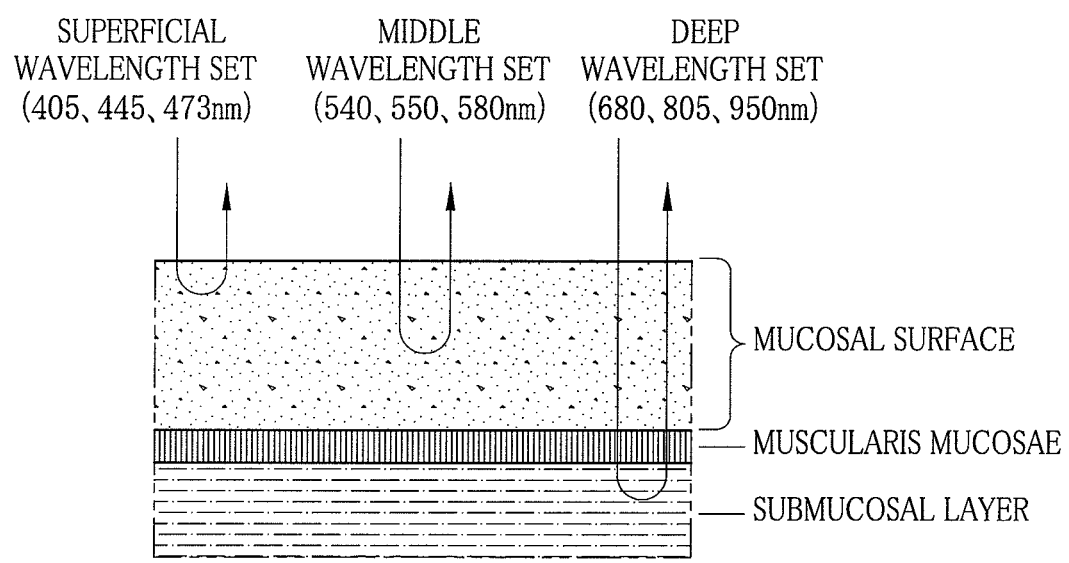
FIG. 10 is an explanatory view showing a depth into which light of each wavelength set penetrates.

The wavelength set switching section 81 chooses one of the wavelength sets each of which includes plural types of narrow band light used for the calculation of the oxygen saturation level, from a wavelength set table 82 of FIG. 9 stored on the ROM 46. In the wavelength set table 82, wavelength sets that are suited for calculation of the oxygen saturation level of the blood vessel at each of superficial, middle, and deep layers are stored in advance. Each wavelength set includes the plural types of narrow band light that adequately penetrate into a target depth. Furthermore, at least one of the plural types of narrow band light has a wavelength band chosen from wavelengths at which the absorption coefficient pa of the oxygenated hemoglobin much differs from that of the deoxygenated hemoglobin. At least another one of the plural types of narrow band light has a wavelength band chosen from wavelengths of the isosbestic points without having the difference in the absorption coefficient μa. By way of example, a superficial wavelength set includes narrow band light of 405 nm (isosbestic point), 445 nm, and 473 nm chosen from a relatively short wavelength band of 400 to 500 nm. A deep wavelength set includes narrow band light of 680 nm, 805 nm (isosbestic point), and 950 nm being near infrared light chosen from a wavelength band of 600 to 1000 nm. A middle wavelength set includes narrow band light of 540 nm, 550 nm, and 580 nm chosen from a wavelength band of 500 to 600 nm. As shown in FIG. 10, the narrow band light of the superficial wavelength set reaches a depth of the order of several tens of micrometers from a surface of mucosa. The narrow band light of the middle wavelength set reaches a depth of several tens to several hundreds of micrometers, which is deeper than the depth the superficial wavelength set reaches. The narrow band light of the deep wavelength set reaches a depth from a muscularis mucosae to a submucosal layer. Note that, each wavelength set includes three types of narrow band light in this embodiment, but may include two or four or more types of narrow band light instead.

Figure 11:
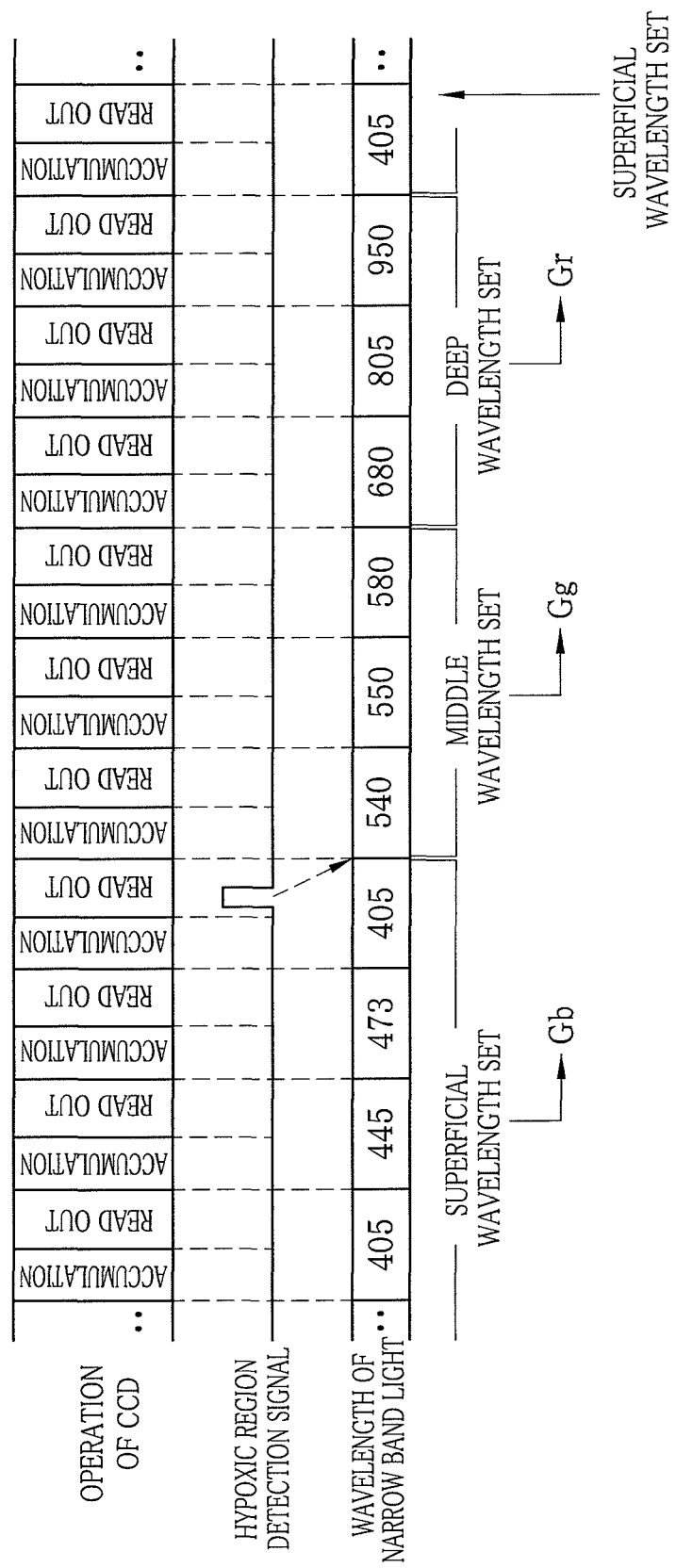
FIG. 11 is a timing chart of switching among the wavelength sets.

As shown in FIG. 11, when the blood information measuring apparatus 2 is put into the special mode by operation of the mode switch 19, the wavelength set switching section 81 chooses the superficial wavelength set as an abnormality detection wavelength set for detecting the hypoxic region (abnormal region). The CPU 66 of the light source device 12 controls operation of the wavelength tunable element 64 such that the three types of narrow band light of the superficial wavelength set are successively emitted in a unit of a charge accumulation period of the CCD 33. Upon input of the hypoxic region detection signal from the comparison section 80, the wavelength set switching section 81 outputs to the CPU 66 signals indicating switching from the superficial wavelength set to the middle wavelength set and switching from the middle wavelength set to the deep wavelength set. Thus, the CPU 66 controls the operation of the wavelength tunable element 64 such that the narrow band light of the middle wavelength set and thereafter the narrow band light of the deep wavelength set are successively emitted in the unit of the charge accumulation period of the CCD 33. After the emission of the narrow band light of the deep wavelength set, the narrow band light of the superficial wavelength set being the abnormality detection wavelength set is applied again. The switching order of the middle wavelength set and the deep wavelength set may be opposite.

An oxygen saturation image Gb is obtained under the narrow band light of the superficial wavelength set, and triggers the output of the hypoxic region detection signal. An oxygen saturation image Gg is obtained under the narrow band light of the middle wavelength set. An oxygen saturation image Gr is obtained under the narrow band light of the deep wavelength set. These oxygen saturation images Gb, Gg, and Gr show information of the oxygen saturation level of the internal body portion, which the comparison section 80 judges to be the hypoxic region, with respect to a depth direction. The display controller 50 displays the oxygen saturation images Gb, Gg, and Gr on the monitor 18 simultaneously in a tiled manner or separately on different screens. The simultaneous display and the separate display may be switched manually or automatically once every predetermined time. This facilitates comparison among the images and smooth diagnosis.

The CPU 45 writes to the ROM 46 or the removable medium the oxygen saturation images Gb, Gg, and Gr in a state of being associated to one another.

As is widely known, cancer tissue induces blood vessel growth (angiogenesis) by secreting various growth factors such as a vascular endothelial growth factor (VEGF), being a major contributor to angiogenesis. The VEGF can induce capillary growth (neovascularization) and increase a blood flow into the cancer tissue, to compensate for a lack of oxygen and other essential nutrients required for the spread or metastasis of the cancer tissue. A neovascular network including newly-formed capillaries grows inward from the cancer tissue and is connected to a thick blood vessel. Thus, the cancer tissue itself has the relatively low oxygen saturation level (hypoxic region), while a region of the newly-formed capillaries surrounding the cancer tissue has the relatively high oxygen saturation level (hyperoxic region).

Figure 12A:
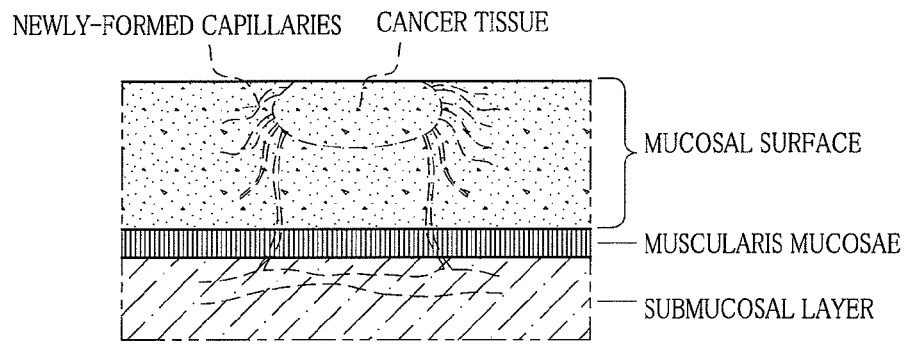
FIG. 12A is an explanatory view showing an example of oxygen saturation images of early cancer captured with light of each wavelength set.
Figure 12A:
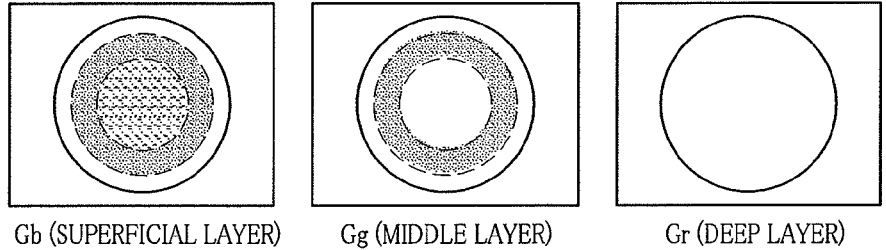

As shown in FIG. 12A, in the case of early cancer the tissue of which is present within a mucosal surface and does not invade the muscularis mucosae, the newly-formed capillaries surround the cancer tissue in the superficial layer and the middle layer. The oxygen saturation image Gb of the cancer tissue and its surroundings shows a hypoxic middle region corresponding to the cancer tissue and a hyperoxic annular region corresponding to the newly-formed capillaries, in general. The oxygen saturation image Gg under the narrow band light of the middle wavelength set shows no region corresponding to the cancer tissue, while shows only a hyperoxic annular region corresponding to the newly-formed capillaries. The oxygen saturation image Gr under the narrow band light of the deep wavelength set shows no variation in the oxygen saturation level.

Figure 12B:
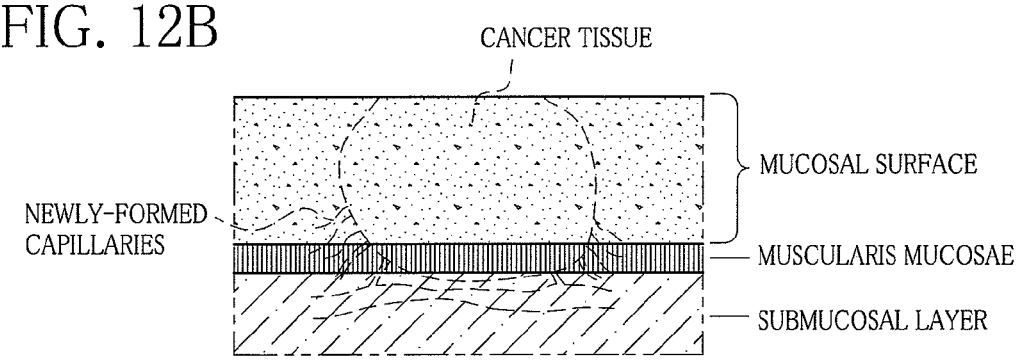
FIG. 12B is an explanatory view showing an example of oxygen saturation images of advanced cancer captured with the light of each wavelength set.
Figure 12B:
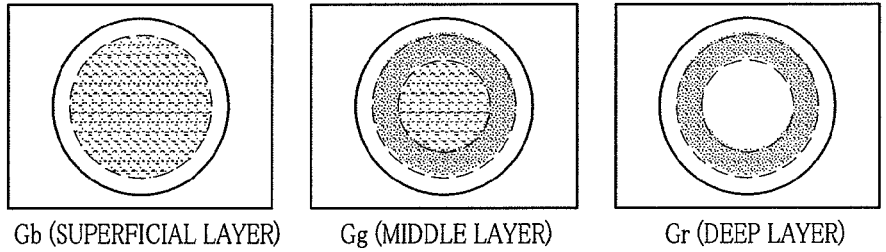

On the other hand, in the case of advanced cancer the tissue of which is spread from the mucosal surface to the submucosal layer, as shown in FIG. 12B, the oxygen saturation image Gb is almost occupied with a hypoxic region corresponding to the cancer tissue. The oxygen saturation image Gg shows a hypoxic middle region corresponding to the cancer tissue and a hyperoxic annular region corresponding to the newly-formed capillaries, as with the oxygen saturation image Gb of FIG. 12A. The oxygen saturation image Gr shows only a hyperoxic annular region corresponding to the newly-formed capillaries.

As described above, the hypoxic and hyperoxic regions shown in the oxygen saturation images Gb, Gg, and Gr vary in accordance with the stage of the cancer. Therefore, observing the oxygen saturation images Gb, Gg, and Gr and analyzing a pattern of the hypoxic and hyperoxic regions allow grasp of the stage (depth) of the cancer.

Next, the operation of the blood information measuring apparatus 2 will be described with referring to FIG. 13. In observing the inside of the patient's body with the electronic endoscope 10, the information related to the patient and the like is inputted and the start of an examination is commanded from the operation unit 48. After the start of the examination, the insert section 13 of the electronic endoscope 10 is introduced into the patient's body. While the inside of the patient's body is irradiated with the illumination light from the light source device 12, the CCD 33 captures the observation image of the inside of the body. The observation image is displayed on the monitor 18.

To be more specific, the image signal outputted from the CCD 33 is subjected to various processes in each component of the AFE 37, and is inputted to the image processor 49. The image processor 49 applies the various image processes to the inputted image signal, and produces the image of the inside of the body. The image processed by the image processor 49 is inputted to the display controller 50. The display controller 50 performs the various display control processes in accordance with the graphic data. Thereby, the observation image is displayed on the monitor 18.

During observation of the inside of the body, an observation mode is switched as necessary. When the insert section 13 of the electronic endoscope 10 is introduced into the patient's body, the normal mode is chosen to carry out insertion operation with a wide view, in other words, while observing the image of the inside of the body captured under the white light. When a lesion that needs detail inspection is found out and the oxygen saturation level of the lesion is obtained, the special mode is chosen to obtain the oxygen saturation images captured with the narrow band light of the appropriate wavelength bands. As necessary, the still image is captured by operating the release button provided on the electronic endoscope 10. When some treatment is required, a necessary medical instrument is inserted into the channel of the electronic endoscope 10 to perform removal of the lesion, administration of a drug, and the like.

In the normal mode, the CPU 45 commands the CPU 66 to turn on the first light source 55, so the white light is applied from the lighting window 31 to the internal body portion.

Figure 13:
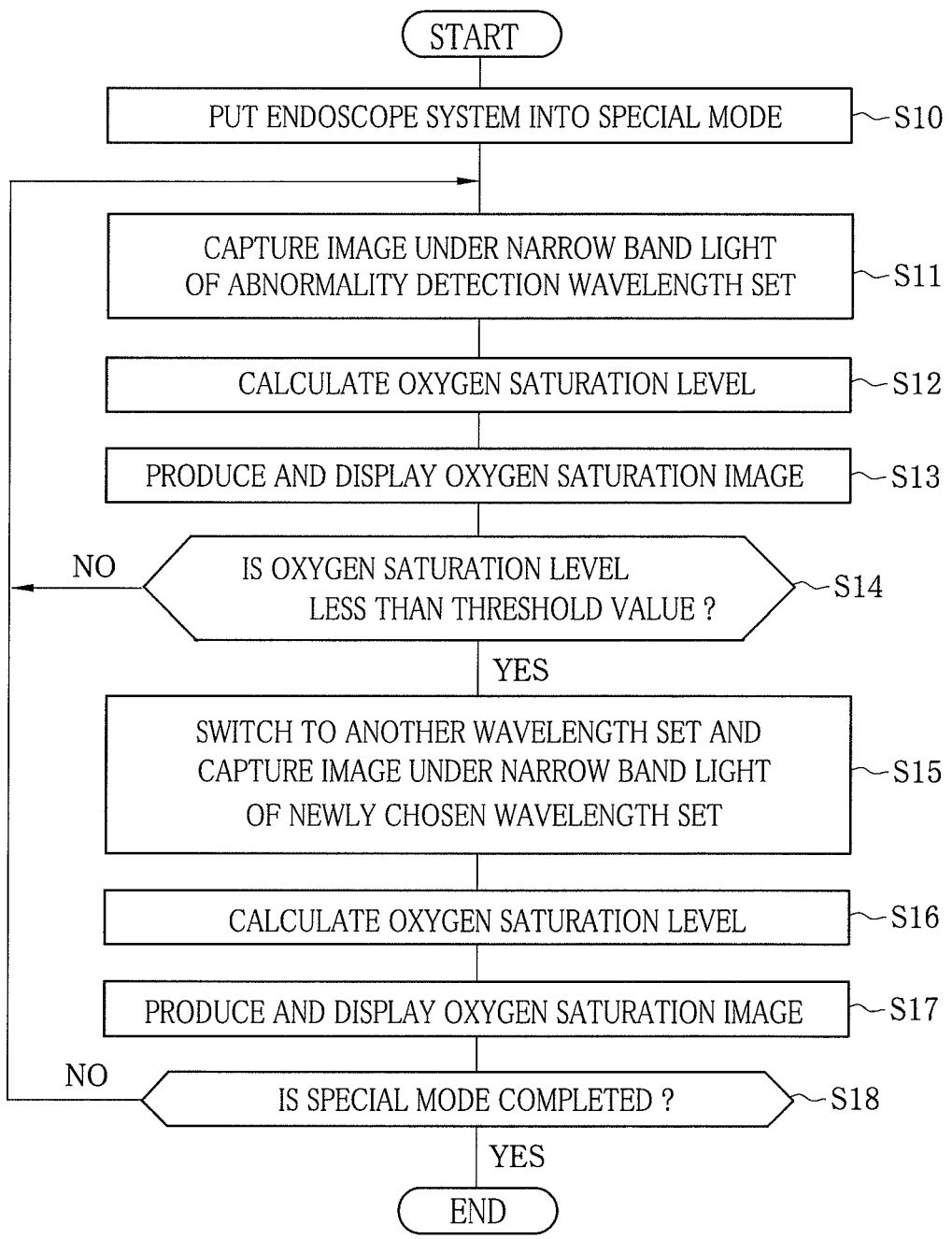
FIG. 13 is a flowchart of an operation process in a special mode.

On the other hand, when the special mode is chosen by operation of the mode switch 19, as shown in S10 of FIG. 13, the wavelength set switching section 81 chooses the superficial wavelength set as the abnormality detection wavelength set. The CPU 66 turns off the first light source 55, and turns on the second light source 56. The CPU 66 controls the operation of the wavelength tunable element 64, such that the three types of narrow band light of the superficial wavelength set are successively emitted in the unit of the charge accumulation period of the CCD 33. The CCD 33 captures the reflected light of the narrow band light of the abnormality detection wavelength set (S11).

In the image processor 49, after the blood vessel area determination section 71 determines the blood vessel area, the blood information calculation section 70 calculates the oxygen saturation level of hemoglobin in the blood vessel based on the reference data 72 (S12). The blood information image production section 73 produces the oxygen saturation image based on the calculation result of the oxygen saturation level. The oxygen saturation image is displayed on the monitor 18 (S13).

The calculation result of the oxygen saturation level is outputted to the CPU 45 of the processor device 11. In the CPU 45, the comparison section 80 compares the calculation result of the oxygen saturation level with the threshold value TH (S14).

When the calculation result of the oxygen saturation level is equal to or more than the threshold value TH (NO in S14), the wavelength set is not changed. The capture of the image under the narrow band light of the superficial wavelength set (S11), the calculation of the oxygen saturation level (S12), and the production and display of the oxygen saturation image (S13) are repeated. On the other hand, when the calculation result of the oxygen saturation level is less than the threshold value TH (YES in S14), the comparison section 80 outputs the hypoxic region detection signal to the wavelength set switching section 81.

In response to input of the hypoxic region detection signal from the comparison section 80, the wavelength set switching section 81 outputs to the CPU 66 a signal for switching to the middle wavelength set and the deep wavelength set in succession. Thus, the CPU 66 controls the operation of the wavelength tunable element 64, so that the three types of narrow band light of the middle wavelength set and the three types of narrow band light of the deep wavelength set are emitted in succession in the unit of the charge accumulation period of the CCD 33. The CCD 33 captures the reflected light of the narrowband light of the middle wavelength set, and then the reflected light of the narrow band light of the deep wavelength set in succession (S15).

As with S12, the blood information calculation section 70 calculates the oxygen saturation level based on image data that is obtained by the CCD 33 capturing the reflected light of the narrow band light of the middle wavelength set and the deep wavelength set (S16). The blood information image production section 73 produces the oxygen saturation images Gb, Gg, and Gr with the narrow band light of the superficial wavelength set, the middle wavelength set, and the deep wavelength set, respectively. The oxygen saturation images Gb, Gg, and Gr are displayed on the monitor 18 simultaneously in a tiled manner or separately on different screens (S17). The oxygen saturation images Gb, Gg, and Gr are related to one another, and written to the ROM 46 and the removable medium. After the emission of the narrow band light of the deep wavelength set, the narrow band light of the superficial wavelength set, being the abnormality detection wavelength set, is emitted again in S11. Above procedure is continued until the special mode is completed (YES in S18) by the choice of the normal mode by operation of the mode switch 19.

As described above, according to the present invention, the oxygen saturation level of the hemoglobin in the blood vessel is calculated from the image data that is obtained under irradiation with the narrow band light of the abnormality detection wavelength set, and the hypoxic region is detected through the comparison between the calculation result and the threshold value TH. When the hypoxic region is detected, the oxygen saturation level is calculated with the narrow band light of each wavelength set by switching among the wavelength sets. Therefore, it is possible to obtain information of the oxygen saturation level in the depth direction from the mucosal surface to the submucosal layer, which facilitates grasping the stage of the cancer, easily and automatically without imposing any load on an operator.

By tracing a history of the oxygen saturation images Gb, Gg, and Gr of a single patient over plural examinations, a growth speed of the cancer can be obtained. This is useful in distinguishing an undifferentiated carcinoma, which rapidly proliferates after metastasis.

At present, in a field of observation of the cancer tissue with the narrow band light, a diagnostic method using an image of capillaries in the superficial surface has been established, and there is an interest in the oxygen saturation level of the capillaries in the superficial surface. For this reason, in this embodiment, the superficial wavelength set is chosen as the abnormality detection wavelength set for detecting the hypoxic region. When the internal body portion to be observed is located in the esophagus or the large intestine, the superficial wavelength set is preferably chosen as the abnormality detection wavelength set.

The abnormality detection wavelength set is not limited to the superficial wavelength set, but the middle wavelength set may be chosen instead. The superficial wavelength set can detect the hypoxic region (cancer tissue) present in the mucosal surface, but is not suited for finding out scirrhous gastric cancer in which a surface of a lesion is sometimes covered with normal tissue, or normal tissue is sometimes left in a lesion in a discrete manner. To find out such scirrhous gastric cancer the hypoxic region of which does not manifest itself in the mucosal surface, the middle wavelength set is preferably chosen as the abnormality detection wavelength set, because the middle wavelength set is suited for calculation of the oxygen saturation level of hemoglobin in a relatively thick blood vessel in the middle of mucosa.

Figure 14:
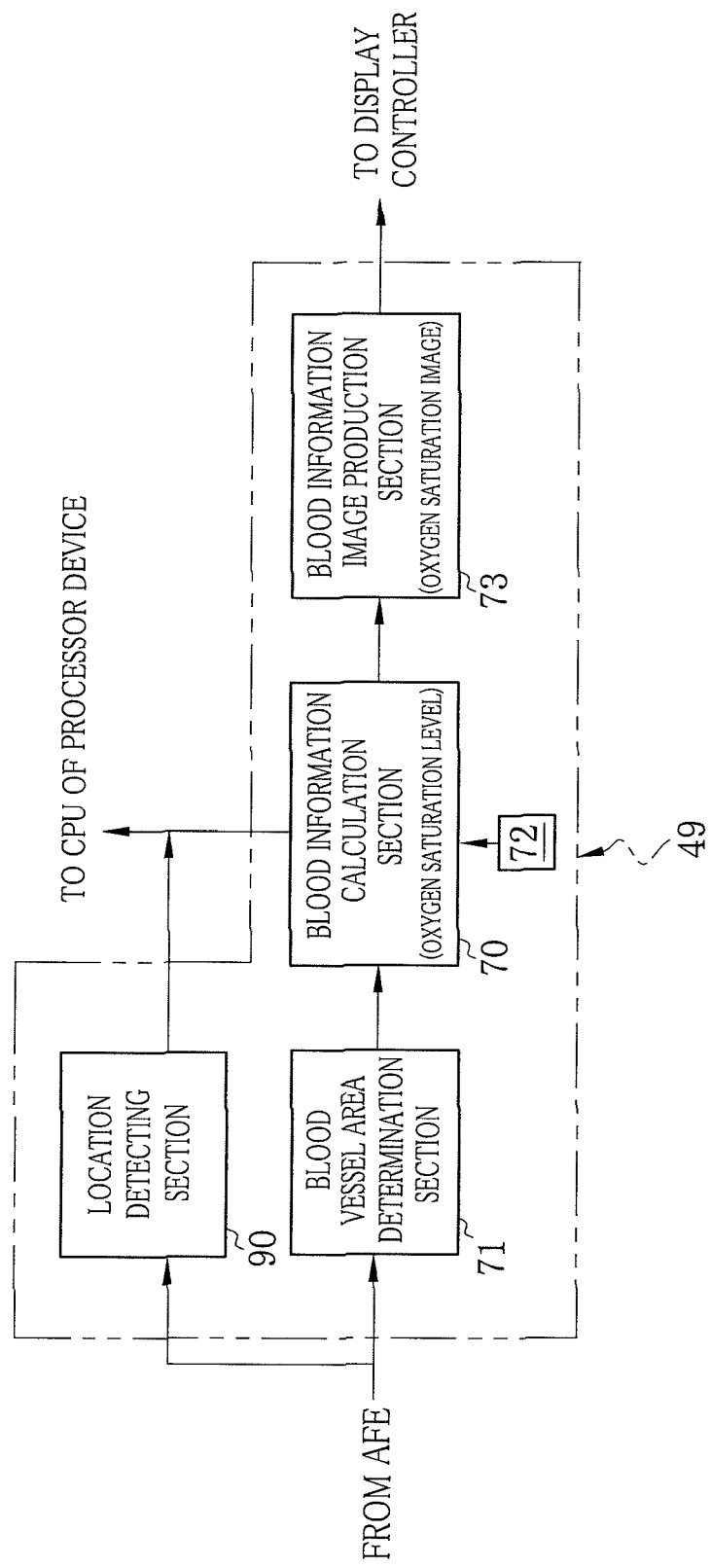
FIG. 14 is a block diagram of an image processor according to a second embodiment.

The abnormality detection wavelength set may be chosen in accordance with a location of the internal body portion to be examined, instead of being fixed at the specific wavelength set. For example, in a case where the electronic endoscope 10 is an esophagogastroduodenoscope, the superficial wavelength set is chosen as the abnormality detection wavelength set when observing esophagus, and the middle wavelength set is chosen as the abnormality detection wavelength set when observing stomach to finding out the scirrhous gastric cancer. The abnormality detection wavelength set may be switched manually by operating a specific operation part provided on the handling section 14 or the like of the electronic endoscope 10. In another case, the image processor 49 may include a location detecting section 90, as shown in FIG. 14. The location detecting section 90 distinguishes whether the internal body portion to be examined is in the esophagus or the stomach by a well-known image recognition technique and the like, and the abnormality detection wavelength set may be automatically switched in accordance with a distinction result.

The image recognition technique includes a method in which the location detecting section 90 may recognize a pattern of cardia of a unique shape positioned in a juncture between the esophagus and the stomach. There is also a method in which the size of a dark section may be compared with a threshold value, because the size of the dark section seen in the image is small during a course from the esophagus to the cardia, while it is large in the stomach. Another method other than the image recognition technique may be available too. For example, the position of the distal end portion 17 of the electronic endoscope 10 may be detected by CT, or the distal end portion 17 may be provided with a pH sensor to use difference in pH between the esophagus and the stomach.

When the middle wavelength set is chosen as the abnormality detection wavelength set, the threshold value TH used in the comparison section 80 is changed to a value specific to the middle wavelength set. Furthermore, if the calculation result of the oxygen saturation level is less than the threshold value TH in the comparison section 80, the wavelength set switching section 81 switches among the wavelength sets from the middle wavelength set to the superficial wavelength set and then to the deep wavelength set. After the calculation of the oxygen saturation level with the deep wavelength set, the middle wavelength set is chosen again. Omitting the switching to the superficial wavelength set, the switching only to the deep wavelength set may be performed.

The wavelength set table 82 of FIG. 9 shows just an example of each wavelength set. Another wavelength set being a combination of other wavelengths may be used in addition to or instead of the wavelength sets shown in the table 82. For example, the mucosal surface may be subdivided into surface, middle, and deep layers, and wavelength sets for the subdivided surface, middle, and deep layers may be prepared.

Instead of the hypoxic region, the hyperoxic region may be detected using the abnormality detection wavelength set, and the wavelength set may be switched in response to the detection of the hyperoxic region.

The special mode may include a mode of obtaining a superficial, middle, or deep blood vessel image (visible image of a blood vessel route) under irradiation with a type of narrow band light having a center wavelength of 450 nm, 550 nm, 780 nm, or the like, a mode of observing fluorescence emitted from the internal body portion by applying excitation light after administration of a fluorescent substance to living body tissue, a mode for observing autofluorescence of living body tissue, and the like.

The wavelength tunable element may be disposed at an exit end of the light guide 34, instead of between the second light source 56 and the light guide 34b. In another case, the wavelength tunable element may be disposed not in a lighting optical system but in an objective optical system for taking the image of the internal body portion, for example, behind the imaging window 30 or on the imaging plane of the CCD 33. Furthermore, instead of provision of the wavelength tunable element, plural light sources each for emitting narrow band light of a specific wavelength band may be provided.

In above embodiments, the oxygen saturation level of the hemoglobin is calculated from the absorbance or concentration being a logarithm of the absorbance, but the blood flow may be calculated from the absorbance or the like. The oxygen saturation level may be calculated at a minute spot, instead of at an area corresponding to an imaging area of the CCD as described above.

The electronic endoscope is used in the above embodiment, but other types of endoscope are available including a fiberscope with an image guide, an ultrasonic endoscope having an imaging device and an ultrasonic transducer at its distal end, and the like. The present invention is applicable to a system that obtains information of the oxygen saturation level and the like by applying the narrow band light to a surface of the patient's body, instead of the inside of the patient's body. In such a case, the insert section to be introduced into the patient's body is unnecessary.

Although the present invention has been fully described by the way of the preferred embodiment thereof with reference to the accompanying drawings, various changes and modifications will be apparent to those having skill in this field.

Therefore, unless otherwise these changes and modifications depart from the scope of the present invention, they should be construed as included therein.

What is claimed is:

1. A blood information measuring apparatus comprising:
   a lighting section for applying illumination light to an internal body portion having a blood vessel;
   an imaging section for performing photoelectric conversion of reflected light from said internal body portion irradiated with said illumination light and outputting an image signal;
      a wavelength tunable element for narrowing a wavelength band of said illumination light to be applied to said internal body portion or said reflected light to be incident on said imaging section in accordance with one of plural wavelength sets;
      a blood information calculation section for calculating blood information of blood flowing through said blood vessel based on said image signal;
      a comparison section for comparing said calculated blood information with a threshold value;
      a wavelength set switching section for controlling said wavelength tunable element so as to switch among said plural wavelength sets in accordance with a comparison result of said comparison section, each of said wavelength sets including plural types of narrow band light that penetrate to similar depths into said internal body portion; and
      a monitor for displaying said blood information measured with each of said wavelength sets,
   wherein said blood information is an oxygen saturation level of hemoglobin calculated based on absorbance,
   wherein
   said wavelength set switching section chooses one of said plural wavelength sets as an abnormality detection wavelength set used for detection of an abnormal region;
   when said oxygen saturation level measured with said abnormality detection wavelength set is less than said threshold value, said comparison section outputs an abnormal region detection signal; and
      said wavelength set switching section switches in response to said abnormal region detection signal from said abnormality detection wavelength set to one of said other wavelength sets, to measure said oxygen saturation level of said blood flowing through said blood vessel at a different depth.

2. The blood information measuring apparatus according to claim 1, wherein said wavelength set includes at least one type of narrow band light having a wavelength at which there is a difference in an absorption coefficient between oxygenated hemoglobin and deoxygenated hemoglobin, and at least one type of narrow band light having a wavelength at which there is no difference in said absorption coefficient between said oxygenated hemoglobin and said deoxygenated hemoglobin.

3. The blood information measuring apparatus according to claim 1, wherein said wavelength set switching section successively switches among said wavelength sets to measure said oxygen saturation level with every said wavelength set, and thereafter chooses said abnormality detection wavelength set again.

4. The blood information measuring apparatus according to claim 1, wherein one of said plural wavelength sets is a superficial wavelength set having said plural types of narrow band light in a blue wavelength band of 400 to 500 nm, and said superficial wavelength set is used as said abnormality detection wavelength set.

5. The blood information measuring apparatus according to claim 1, further comprising a location detecting section for detecting a location of said internal body portion within a body, an abnormality detection wavelength set being chosen from said plural wavelength sets in accordance with said location.

6. The blood information measuring apparatus according to claim 5, wherein said location detecting section detects said location of said internal body portion within said body by applying an image recognition process to an image of said internal body portion.

7. The blood information measuring apparatus according to claim 5, wherein
   said plural wavelength sets include a superficial wavelength set having said plural types of narrow band light in a blue wavelength band of 400 to 500 nm, and a middle wavelength set having said plural types of narrow band light in a green wavelength band of 500 to 600 nm;
   when said location detecting section detects that said internal body portion is located in esophagus or large intestine, said superficial wavelength set is chosen as said abnormality detection wavelength set; and
   when said location detecting section detects that said internal body portion is located in stomach, said middle wavelength set is chosen as said abnormality detection wavelength set.

8. The blood information measuring apparatus according to claim 7, wherein said wavelength sets include a deep wavelength set having said plural types of narrow band light in a red wavelength band of 600 to 1000 nm.

9. The blood information measuring apparatus according to claim 1, wherein
   said lighting section emits white light in a broad wavelength band as said illumination light; and
   said wavelength tunable element is disposed in said lighting section to narrow said wavelength band of said illumination light, or is disposed in said imaging section to narrow said wavelength band of said reflected light.

10. The blood information measuring apparatus according to claim 1, wherein said monitor displays calculation results of said oxygen saturation level obtained with switching among said plural wavelength sets simultaneously in a tiled manner or separately on different screens on a wavelength set basis.

11. The blood information measuring apparatus according to claim 1, further comprising a mode switch for switching between a normal mode and a special mode, wherein
   in said normal mode, white light in a broad wavelength band is applied to said internal body portion, and an image is produced from said image signal obtained under said white light and displayed on said monitor; and
   in said special mode, said oxygen saturation level is calculated, and a calculation result is displayed on said monitor.

12. A blood information measuring method comprising the steps of:
   applying illumination light to an internal body portion;
   performing photoelectric conversion of reflected light from said internal body portion irradiated with said illumination light, and outputting an image signal;
   narrowing a wavelength band of said illumination light to be applied to said internal body portion or said reflected light in accordance with one of plural wavelength sets;
   calculating blood information of blood flowing through a blood vessel based on said image signal;

comparing said calculated blood information with a threshold value; and switching among said plural wavelength sets in accordance with a comparison result, each of said wavelength sets including plural types of narrow band light that penetrate to similar depths into said internal body portion, wherein said blood information is an oxygen saturation level of hemoglobin calculated based on absorbance, wherein said wavelength set switching step chooses one of said plural wavelength sets as an abnormality detection wavelength set used for detection of an abnormal region;

when said oxygen saturation level measured with said abnormality detection wavelength set is less than said threshold value, said comparison step outputs an abnormal region detection signal; and said wavelength set switching step switches in response to said abnormal region detection signal from said abnormality detection wavelength set to one of said other wavelength sets, to measure said oxygen saturation level of said blood flowing through said blood vessel at a different depth.

13. The blood information measuring method according to claim 12, wherein said blood information is an oxygen saturation level of hemoglobin calculated based on absorbance.

* * * * *